United States Patent [19]
Gilson

[11] Patent Number: 5,904,703
[45] Date of Patent: May 18, 1999

[54] OCCLUDER DEVICE FORMED FROM AN OPEN CELL FOAM MATERIAL

[75] Inventor: Paul Gilson, Moycullen, Ireland

[73] Assignee: Bard Connaught, Dublin, Ireland

[21] Appl. No.: 08/967,361

[22] Filed: Nov. 7, 1997

[51] Int. Cl.⁶ .................................................. A61B 17/04
[52] U.S. Cl. ............................................................ 606/213
[58] Field of Search .................................. 606/213, 215, 606/216, 217, 151, 153, 191, 198; 604/167, 281; 600/32; 128/899

[56] References Cited

U.S. PATENT DOCUMENTS

| | | | |
|---|---|---|---|
| 4,869,268 | 9/1989 | Yoon | 606/131 |
| 5,108,420 | 4/1992 | Marks . | |
| 5,171,259 | 12/1992 | Inoue . | |
| 5,192,301 | 3/1993 | Kamiya et al. | 606/213 |
| 5,258,000 | 11/1993 | Gianturco | 606/215 |
| 5,284,488 | 2/1994 | Sideris | 606/213 |
| 5,334,217 | 8/1994 | Das . | |
| 5,366,478 | 11/1994 | Brinkerhoff et al. | 606/213 |
| 5,433,727 | 7/1995 | Sideris . | |
| 5,634,936 | 6/1997 | Linden et al. | 606/213 |
| 5,634,937 | 6/1997 | Mollenauer et al. | 606/213 |
| 5,667,513 | 9/1997 | Torrie et al. | 606/151 X |
| 5,702,421 | 12/1997 | Schneidt . | |
| 5,741,297 | 4/1998 | Simon | 606/215 X |

FOREIGN PATENT DOCUMENTS

| | | |
|---|---|---|
| 0362113 | 4/1990 | European Pat. Off. . |
| 0 815 794 A1 | 7/1998 | European Pat. Off. . |
| 2 714 284-A1 | 6/1995 | France . |
| 2269321 | 2/1994 | United Kingdom . |
| WO-A-9219162 | 11/1992 | WIPO . |
| WO 95/28885 | 11/1995 | WIPO . |

*Primary Examiner*—Michael Buiz
*Assistant Examiner*—Vikki Trinh
*Attorney, Agent, or Firm*—Morgan & Finnegan, L.L.P.

[57] ABSTRACT

A transcatheter occluder device for closing an opening in a tissue wall includes a body member formed of an open cell polymer foam capable of holding a predetermined occluder shape and being resiliently compressible for transcatheter deployment. The occluder device includes a pair of spaced-apart disks interconnected by a narrow neck portion. Grip means are provided in the neck portion to releasably engage a guide wire for deployment of the occluder device through a catheter.

14 Claims, 9 Drawing Sheets

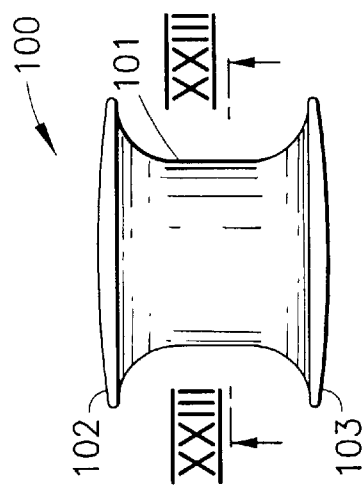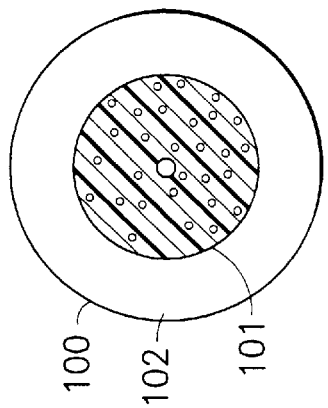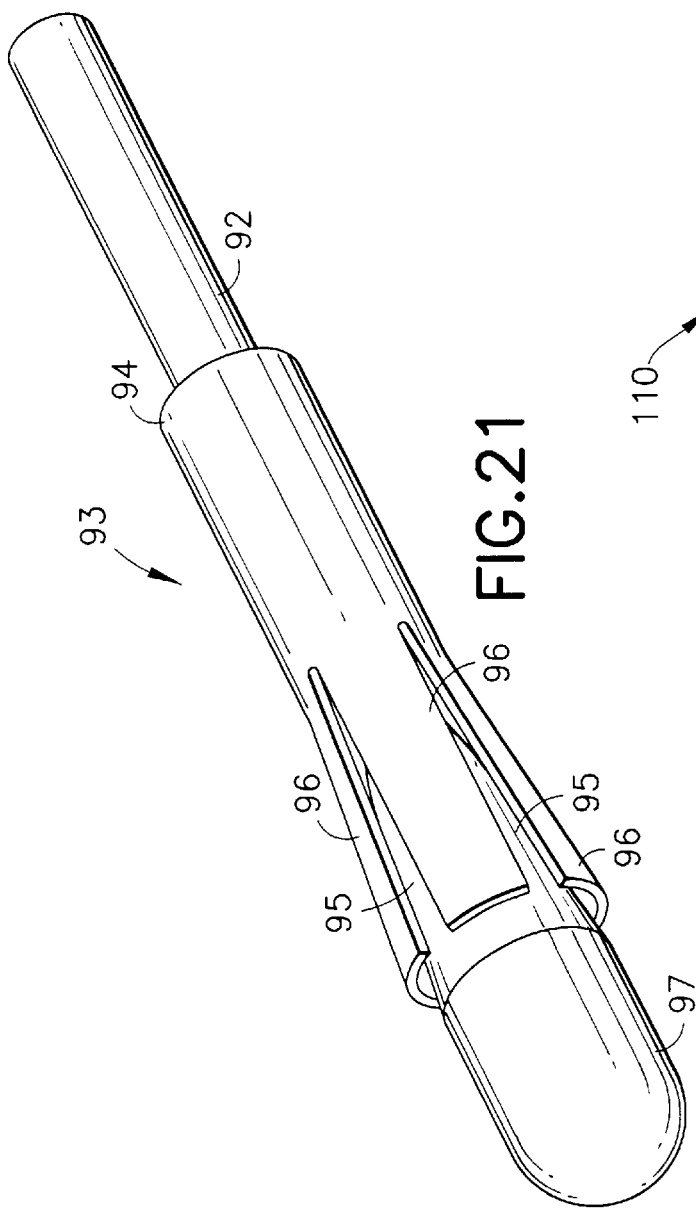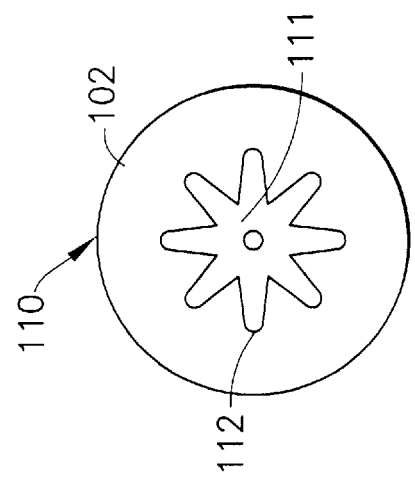

OCCLUDER DEVICE FORMED FROM AN OPEN CELL FOAM MATERIAL

The invention relates to an occluder device for the repair of cardiac defects and the like in humans or animals.

The occluder device is primarily targeted at but not limited to coronary applications. It is envisioned that a significant number of other physiological conditions may be treated with occluder devices according to the invention.

The invention particularly relates to a device for delivery transarterially or transvenously for occluding sepal defects or shunts in the heart or the vascular system.

A known type of occluder device is disclosed in patent specification no. WO 95\28885. The device has a pair of occluder disks interconnected by a string which allows adjustment of the space in between the disks to accommodate different wall thicknesses at the defect. The disks are essentially clamped together across the opening or defect. Each of the occluder disks is formed by polyurethane foam or woven material mounted on a folding wire frame.

U.S. Pat. No. 5,433,727 discloses an occluder device for repair of large heart defects. The device has an occluder disk and an associated counter-occluder. The occluder disk is formed by foldable polyurethane foam attached to a wire skeleton. The counter-occluder comprises a pair of wires forming a pyramid-shaped cage attached to the occluder disk. The wires engage sides of a defect to center the occluder disk at the defect.

In European Patent Specification No. 0362113 there is disclosed a device for occluding cardiac defects. The device has an occluder disk and an associated counter-occluder for deployment at opposite sides of a defect. The occluder and counter-occluder each comprise foldable polyurethane foam mounted on a wire skeleton.

U.S. Pat. No. 5,192,301 discloses a device for closure of medical defects having a flanged design that is formed from a shape memory polymer with a recovery temperature of between 20 and 70° C. The Patent Specification describes a molded plug that is deformed to a reduced size and then cooled to set the shape prior to insertion. The device is then inserted into the defect and heated to its transition temperature. This heating has the effect of allowing the plug to regain its original shape and provide for closure of the defect by a flange of the device.

U.S. Pat. No. 5,284,488 discloses a device having a distal occluder and a proximal occluder connected by string for deployment at opposite sides of a defect. Pulling the string moves the occluders together for spacing adjustment between the occluders or the occluders may be joined by elastic to accommodate different thicknesses of tissue at the defect. Again the occluders comprise polyurethane foam or woven material mounted on a wire skeleton.

GB 2269321 shows an occluder device having umbrella-like disks formed by a web stretched on the frame. The frame elements are sprung to increase the grip of the device at the defect especially where the defect is in thin-walled tissues. The frame elements are curved to improve grip.

U.S. Pat. No. 5,334,217 discloses an occluder device having a pair of occluding disks, each disk comprising a membrane on an elastically deformable frame which extends around a periphery of the defect.

U.S. Pat. No. 5,171,259 discloses an occluder device having a pair of disks each comprising a foldable annular frame with cloth stretched over the frame. The disks are interconnected by thread which when pulled draws the disks together on opposite sides of the opening to bridge the opening.

The known occluder devices generally comprise a pair of interconnected disks each having a collapsible rigid frame, typically of stainless steel wire or nitinol across which a membrane or web of material is stretched. The devices are deployed in a defect with one of the disks on each side of the defect opening to close the opening by means of the disks.

A problem with the known devices is that the rigidity imparted to the membrane or web by the frame can lead to an imperfect fit in many cases, resulting in residual leakage past the device. Also, metal frames subjected to cyclical fatigue loads such as occur in cardiac applications can fail. Another problem with metal frames is their electrical conductivity which can cause problems particularly in cardiac applications.

Also, because of their size and rigidity they cannot be used in many cases due to the proximity of other important cardiac structures. Further, in many cases the known occluder devices require relatively large delivery systems which makes them unsuitable for treatment of small children.

The present invention is directed towards overcoming these problems.

It is an object of the invention to improve the performance of the catheterization or surgical procedure whereby a device is implanted to allow the correction of a range of medical conditions relating to the shunts, or flow pathways that are undesirable, for example, ASD (atrial septal defect), PDA (patent ductus arteriosus) and PFO (patent foramen ovale). The device will be functional in non-coronary applications also, by tailoring the shape to the anastomosis requiring closure, for example, bowel fistulas that currently require surgical intervention. Similarly, a configuration of the device can be used for pre-operative vasoocclusion and site specific flow reduction to abnormalities in the vascular system such as arteriovenous malformations, arteriovenous fistulas or other vascular aneurysms.

According to the invention there is provided a transcatheter occluder device for closing an opening in a tissue wall or a vessel wall, the device comprising:

a body member formed from a material which is self-supporting to hold a desired occluder shape but is resiliently compressible for transcatheter deployment;

the body member being formed of or at least coated with a biologically compatable material;

the body member having means for closing the opening; and the body member having means for retaining the body member in the opening.

In one embodiment of the invention the device comprises a body member formed from a material which is self-supporting to hold a desired occluder shape but is resiliently compressible for transcatheter deployment, the body member being formed of or at least coated with a biologically compatible material, the body member having means for engaging a side edge of the opening for centering the body member in the opening, and the body member having means for retaining the body member in the opening.

The body can be formed from a range of compressible bio-compatible, bio-stable or bio-resorbable polymeric materials. Preferably, the body is formed of a compressible polymer foam or porous structure. Thus advantageously the device can be readily easily loaded in a compressed condition in a delivery catheter for deployment at a defect and once in position at the defect, its flexibility allows it to accommodate to the contours of the tissue walls surrounding the defect for a snug and accurate fit.

In a preferred embodiment at a least portion of a periphery of the body member is engagable with the side edge of the opening. Thus the device will be centered in the defect.

Conveniently the cross-sectional area of the body is equal to or greater than the cross-sectional area of the opening.

In another embodiment the body member is shaped to correspond to the shape of the opening.

In a further embodiment the body member has a cylindrical shape.

In another embodiment the body member has a number of outwardly projecting ribs on a surface of the body member, said ribs being engagable with the edge of the opening in use.

In a preferred embodiment the retaining means comprises a pair of disks each of larger size than the opening, a disk being mounted at each end of the body member.

In another embodiment the retaining means comprises a plurality of retaining fingers extending laterally outwardly at each end of the body member. This reduces the amount of material in the device to facilitate compaction for deployment.

In a particularly preferred embodiment the body member is formed from an open cell polymer foam material.

In another embodiment the device incorporates radiopaque means to facilitate viewing of the device during deployment.

In a further embodiment the body member has grip means engagable with an associated guide wire for movement of the device through a catheter for deployment.

Conveniently the grip means is a tubular sleeve mounted in the body member which is engagable by an associated clamp on the guide wire, said clamp comprising a split collar through which the guide wire passes and an enlarged head at an outer end of the guide wire which is moveable through the collar to expand the collar for releasable clamping engagement within the sleeve of the body member.

In another embodiment the grip means is a bulbous lug on the body member which is releasably engagable by an associated collet at an outer end of the guide wire.

In a further embodiment the grip means is an eye on the body member releasably engagable by an associated hook or pin at an outer end of the guide wire.

The invention will be more clearly understood by the following description of some embodiments thereof, given by way of example only, with reference to the accompanying drawings, in which:

FIG. 21 is a detail perspective view of a gripper system for gripping the occluder device for deployment;

FIG. 22 is a elevational view of another occluder device;

FIG. 23 is a sectional view taken along the line XXIII—XXIII of FIG. 22; and

FIG. 24 is a view similar to FIG. 23 of another occluder device.

Figure 1A:
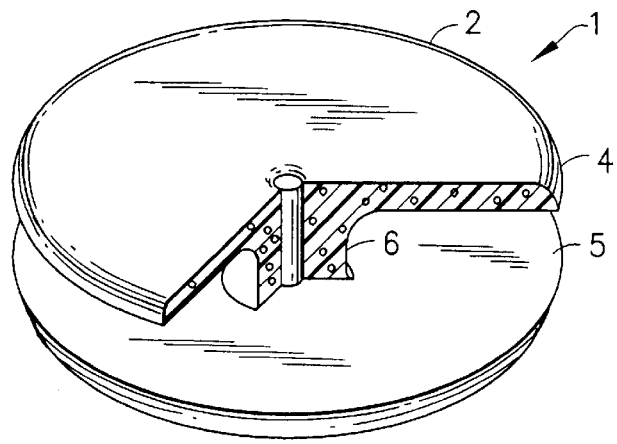
FIG. 1a is a perspective partially cut-away view of an occluder device according to the invention.
Figure 1B:
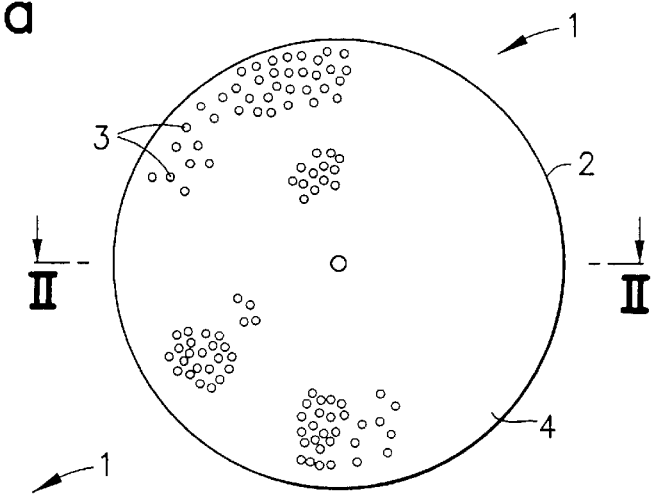
FIG. 1b is an elevational view of the occluder device.
Figure 2:
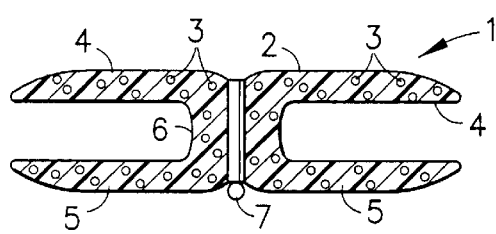
FIG. 2 is a sectional elevational view taken along the line II—II of FIG. 1b.

Referring to the drawings, and initially to FIGS. 1 and 2, there is illustrated an occluder device according to the invention and indicated generally by the reference numeral 1. The device 1 has a body 2 formed of a compressible polymeric foam with an open cell structure. A plurality of voids 3 within the foam of the body 2 render it highly compressible and flexible. The body has a pair of spaced-apart disks 4, 5 interconnected by a narrowed neck portion 6 extending between the disks 4, 5. Grip means indicated generally by the reference numeral 7 is mounted centrally within the neck portion 6, the grip means 7 being used for deployment of the device 1 in use as will be described later.

Figure 3:
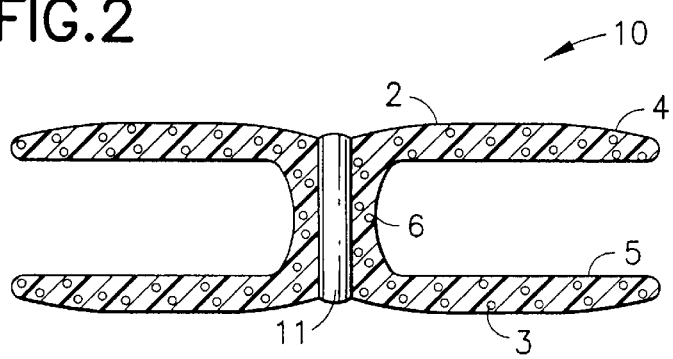
FIG. 3 is a view similar to FIG. 2 of another occluder device.

Referring to FIG. 3, there is illustrated another occluder device 10 in which parts similar to those described for the occluder device of FIGS. 1 and 2 are assigned the same reference numerals. In this case, the grip means 7 comprises a tubular sleeve 11 which forms a central axis to which the body 2 can be bonded. The sleeve 11 incorporates some dense materials to provide indication of radiopacity in order to deploy the device under fluoroscopy or alternative diagnostic imaging system. It is envisioned that several configurations are possible. For example, radiopaque bands may be bonded top and bottom to the sleeve 11 or a continuous wound spring or tube can form the sleeve 11. Alternatively, a spring or tube could be attached to the sleeve 11. It will be noted that the central location of the sleeve within the foam of the body 2 ensures the sleeve is insulated by the foam.

The body 2 has a 3-dimensional resiliently compressible polymeric structure. Compressibility is achieved by providing voids 3 from which air or fluid can be removed by compression, as in an open cell foam or other porous structure. The device can be formed or shaped in a number of ways, known in the public domain. They include injection molding, foam cutting, forming and casting. The shape of the body will depend on the morphology of the site being targeted for closure. Tailoring can be achieved by appropriately dimensioning the mold tooling or by cutting or thermal shaping processes. The resulting shape may or may not be symmetrical as appropriate, however, the shape will result in an arrangement such that once implanted, it would need to be deformed prior to removal. Its structural integrity and stiffness properties will ensure that once deployed, it will remain in place postoperatively. Also, once in place, the body's reaction will initiate a mechanism of endothelial coverage of the device that will further enhance its anchorage at the deployment site.

The device is designed to include a grip means 7 provided by a mechanism or protrusion that will allow secure attachment to a delivery system during placement and allow it to be remotely detached from the delivery catheter once the required position has been reached.

During the interventional procedure, the aim firstly is to locate the vascular anomaly through a diagnostic imaging procedure. This may include fluoroscopy, ultrasonic imaging, magnetic resonance imaging or alternative imaging method. Once located and visualised, an appropriately sized device 1 is selected. The device 1 is compressed, typically into a cylindrical, elliptical or other appropriate shape (see FIG. 4) and then loaded into a catheter. Under-fluoroscopic control, the device delivery system is maneuvered transarterially or transvenously to the required position at a defect opening. A distal end of the device 1 is advanced through the defect opening and the delivery sheath is retracted to allow an outer disk 4 of the device 1 to regain its neutral shape. It will then be positioned on the distal side of the opening and the proximal side disk 5 will be allowed to open by further withdrawal of the sheath. The user will confirm that they are satisfied with the location before releasing the prosthesis from the delivery catheter. If the position is not the desired or optimal one, the sheath can be moved distally to reposition the device 1 in the sheath arrangement at which time it may be removed and repositioned or removed completely from the patient.

Figure 4:
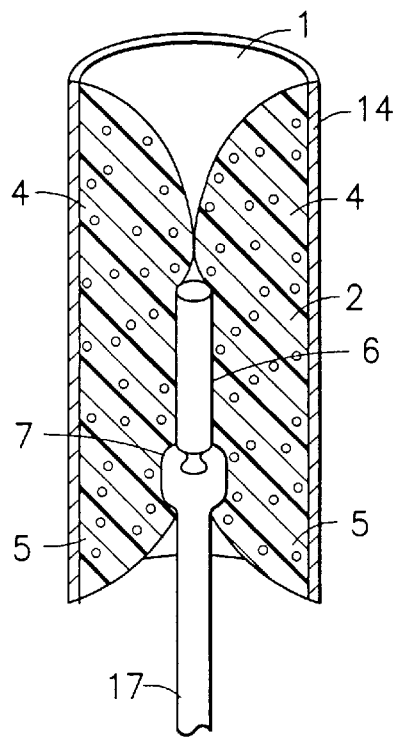
FIG. 4 is a sectional elevational view of the occluder device mounted in a compressed configuration within a loading tube for deployment through a catheter.

FIG. 4 shows the device 1 mounted in a loading tube 14 for mounting in a catheter for deployment. A guide wire attachment 17 grips the device 1 for manipulation and deployment of the device 1.

Figure 6:
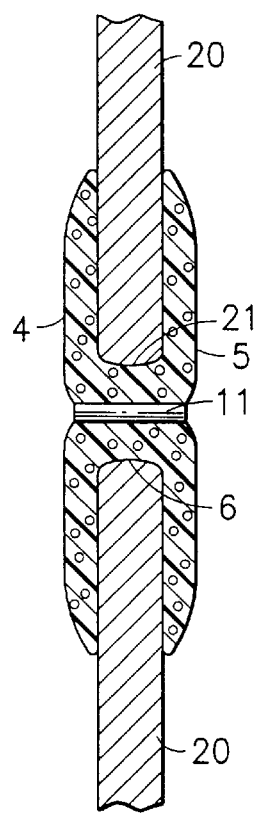
FIG. 6 is a sectional elevational view showing the device mounted in a tissue wall correcting a defect.
Figure 5:
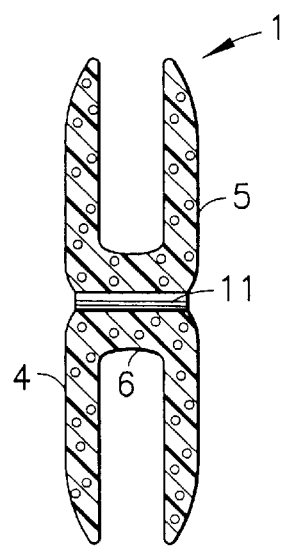
FIG. 5 is a sectional elevational view of the device.

FIG. 5 shows a sectional elevational view of the device 1 in a neutral state. FIG. 6 shows the device 1 in position mounted in a tissue wall 20 occluding a defect opening 21. As can be seen, the neck 6 sits in the defect opening 21 and the disks 4, 5 engage faces of the tissue wall 20 on opposite sides of the opening 21. It will be noted that the compressibility of the material allows the disks 4, 5 to closely follow the contour of the walls for a tight and accurate fit. Preferably, the cross-sectional area of the neck 6 is the same or greater than the cross-sectional area of the defect opening for a snug fit or interference fit centering the device 1 in the opening 21.

Figure 7:
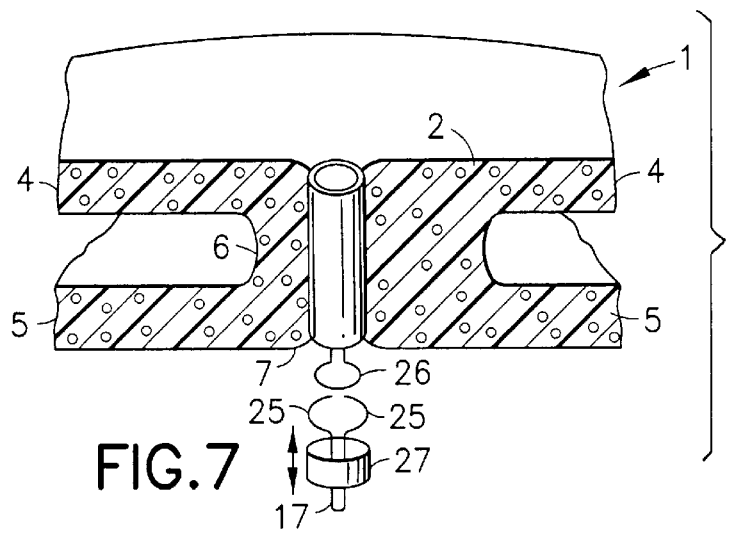
FIG. 7 is a detail partially sectional perspective view of portion of the device showing a gripping system for holding the device.
Figure 8:
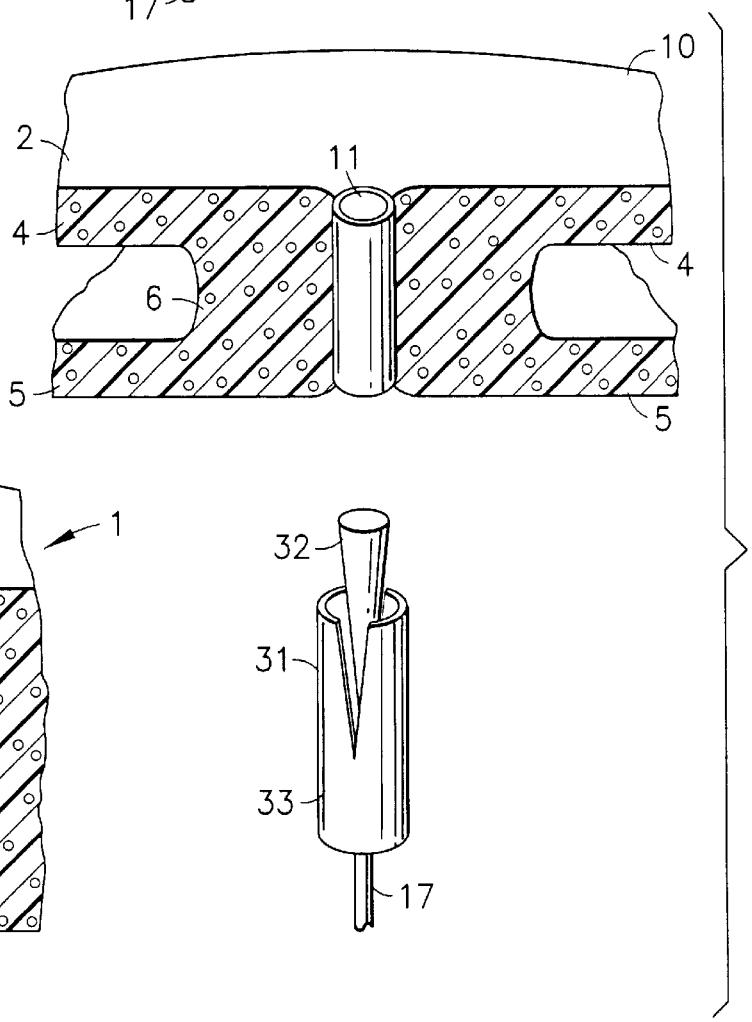
FIG. 8 is a view similar to FIG. 7 showing another device with an alternative gripping system.
Figure 9:
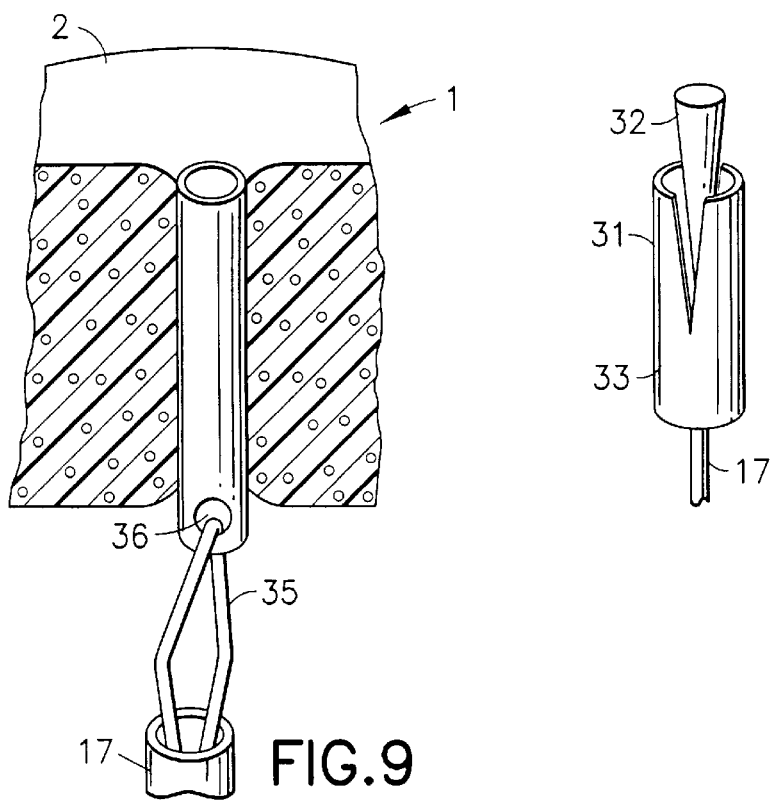
FIG. 9 is a view similar to FIG. 7 of a further device with another gripping system.

FIGS. 7, 8 and 9 show different gripping methods for holding the device 1, 10 by means of the attachment 17. FIG. 7 shows a collet arrangement whereby a pair of collet arms 25 at a free end of the attachment 17 can be opened to grip a complementary lug 26 on the device 1. The collet arms 25 can be clamped about the lug 26 by means of a remotely operable sliding collar 27 on the attachment 17.

FIG. 8 shows an alternative arrangement whereby a tubular sleeve 11 on the device 10 is engagable by means of an expandable head 31 at a free end of the attachment 17. The expandable head 31 has axially slidable tapered elements 32, 33. With the tapered elements 32, 33 in the position shown, the head 31 can be inserted in the sleeve 11. Upon retraction of the inner tapered element 32 within the outer tapered element 33, the outer tapered element 33 is expanded to grip within a bore of the sleeve 11.

FIG. 9 shows a wire or pin release mechanism 35 at the end of the attachment 17 for gripping an associated eye 36 in the device 1.

Figure 10:
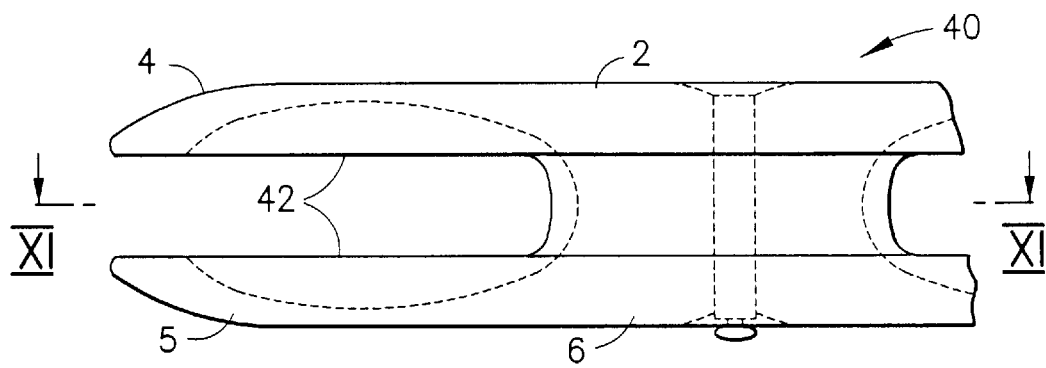
FIG. 10 is a detail elevational view of another occluder device.
Figure 11:
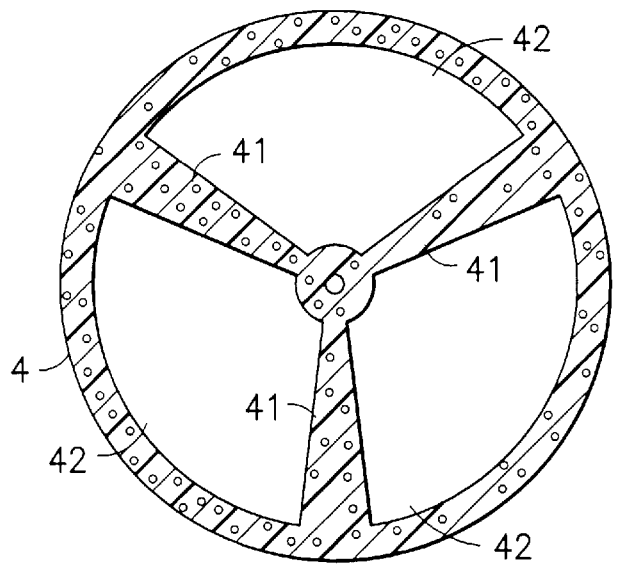
FIG. 11 is a sectional view taken along the line XI—XI of FIG. 10.

FIG. 10 shows another occluder device 40 in which parts similar to those described previously are assigned the same reference numerals. In this case, each disk 4, 5 is formed with a number of integrally molded support struts 41, with foam material between the struts 41 cut away leaving slots or grooves 42. The removal of material facilitates compression of the device for deployment.

Figures 12, 13:
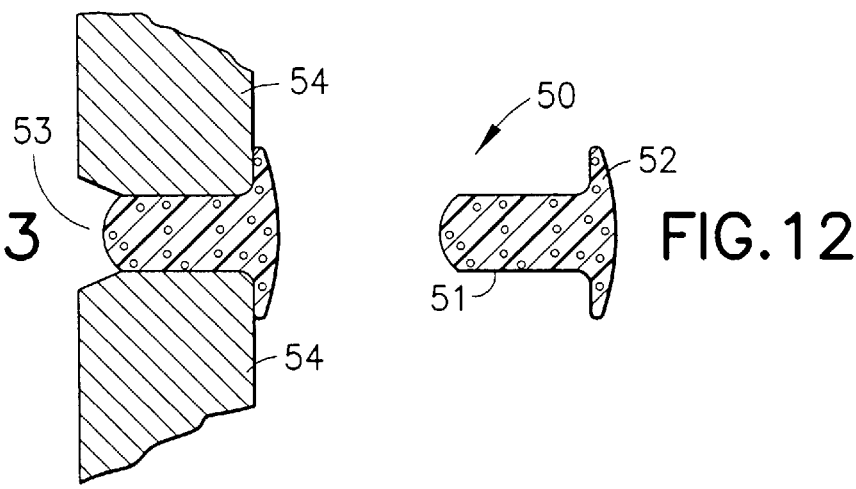
FIG. 12 is a sectional elevational view of another occluder device.
FIG. 13 is a sectional elevational view of the occluder device of FIG. 12 shown in use.

Referring to FIGS. 12 and 13, there is shown another configuration of occluder device 50. The occluder device 50 has a foam body having a generally cylindrical body portion 51 with a flange or disk 52 at one end of the body 51. FIG. 13 shows the device 50 mounted within an opening 53 of a tissue wall 54, the body 51 being in compression when it is mounted in the opening 53 for anchoring the device 50 in the opening 53.

Figure 14:
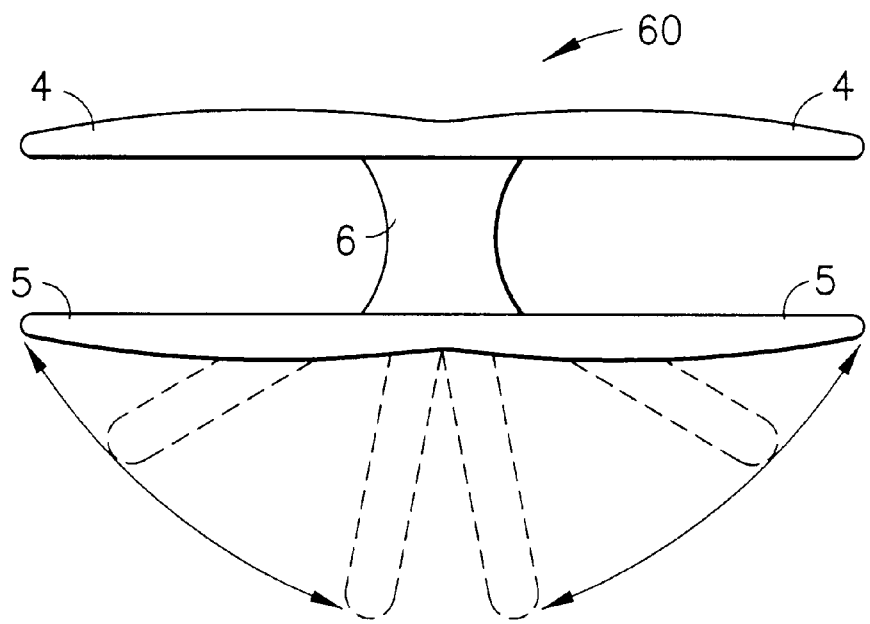
FIG. 14 is an elevational view of another occluder device.

Referring to FIG. 14 there is shown another occluder device according to the invention indicated generally by the reference numeral 60. Parts similar to those described previously are assigned the same reference numerals. In this case the folding of the occluder device 60 is shown in broken outline, each of the disks 4, 5 being folded to essentially form an extension of the neck portion 6. When folded the device 60 can be loaded in a catheter for deployment.

Figure 15:
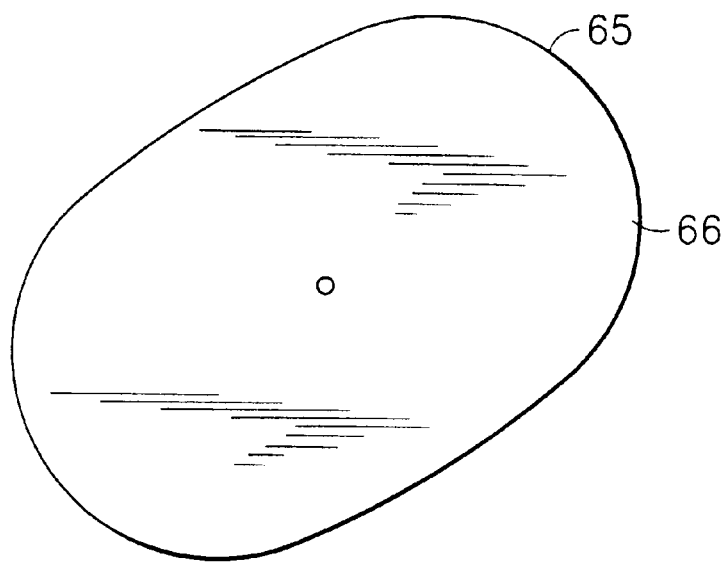
FIG. 15 is a plan view of a further occluder device.
Figure 16:
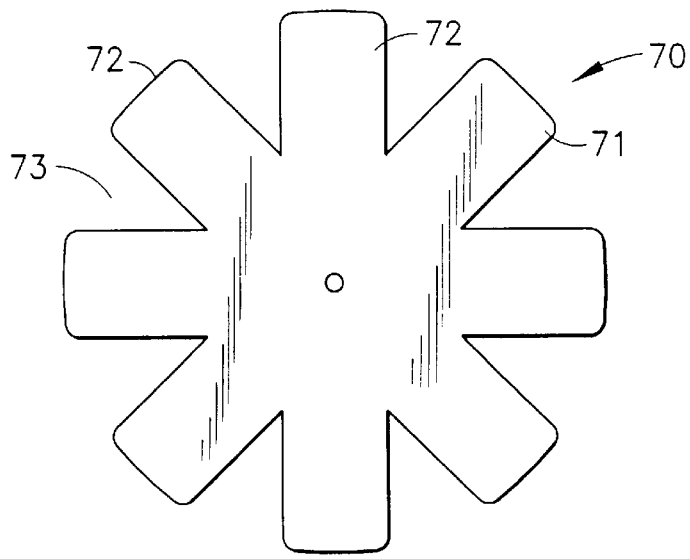
FIG. 16 is a plan view of a still further occluder device.

While the disks 4, 5 in the devices described previously have been essentially circular, the disks 4, 5 may be of any suitable shape. For example, FIG. 15 shows another occluder device 65 having disks 66 which are generally elliptical in shape. FIG. 16 shows an occluder device 70 having disks 71 formed essentially by radial fingers 72. Advantageously slots 73 formed by cutting away material between the fingers 72 facilitate the collapsing of the disks 71 into a compact configuration for delivery through a catheter.

Figure 17:
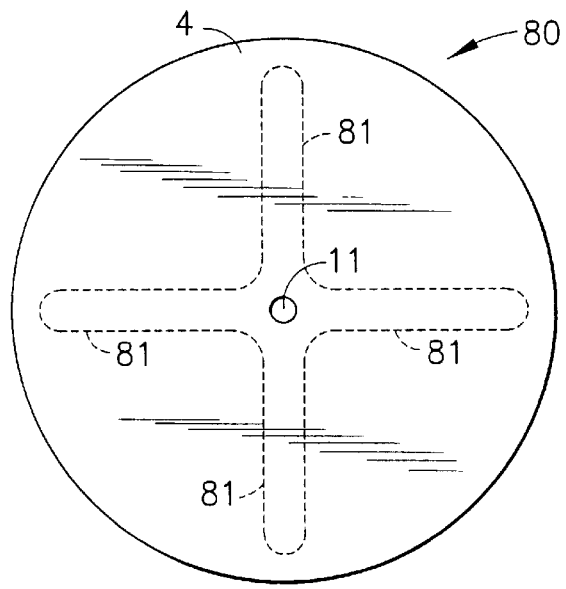
FIG. 17 is a plan view of another occluder device.
Figure 18:
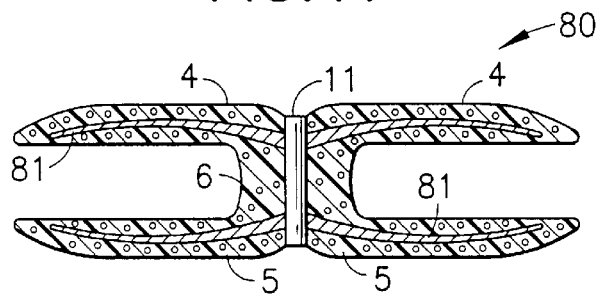
FIG. 18 is a sectional elevational view of the occluder device of FIG. 17.

Referring to FIGS. 17 and 18 there is shown another occluder device indicated generally by the reference numeral 80. Parts similar to those described previously are assigned the same reference numerals. In this case a number of stiff arms 81 are embedded in each disk 4, 5 and extend radially outwardly from the sleeve 11. The arms 81 provide support for the disks 4, 5, the arms 81 being of stronger material than the foam substrate of the disks 4, 5. At the same time, the arms 81 are sufficiently flexible to allow folding along the axis of the sleeve for compaction and loading in a catheter for deployment. Advantageously the use of the reinforcing arms 81 allows less foam to be used or a more compressible foam to be used to facilitate minimising the size of the device 80 when it is compacted for insertion through a catheter.

Figure 19:
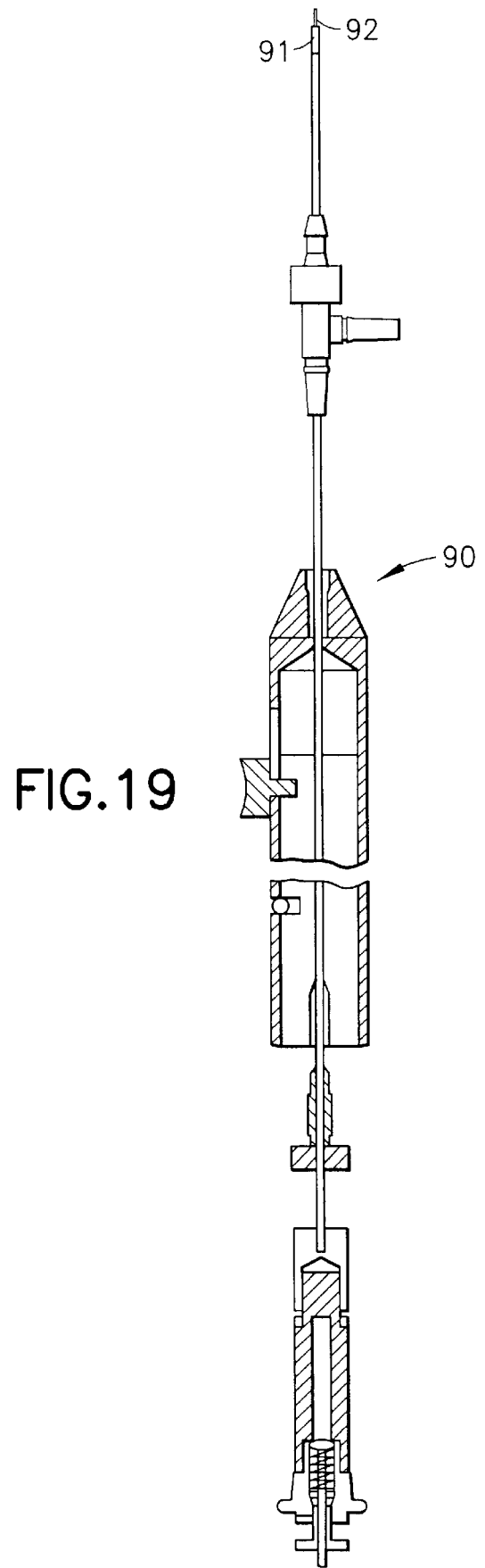
FIG. 19 is a sectional elevational view of an implant device for deployment of the occluders.
Figure 20:
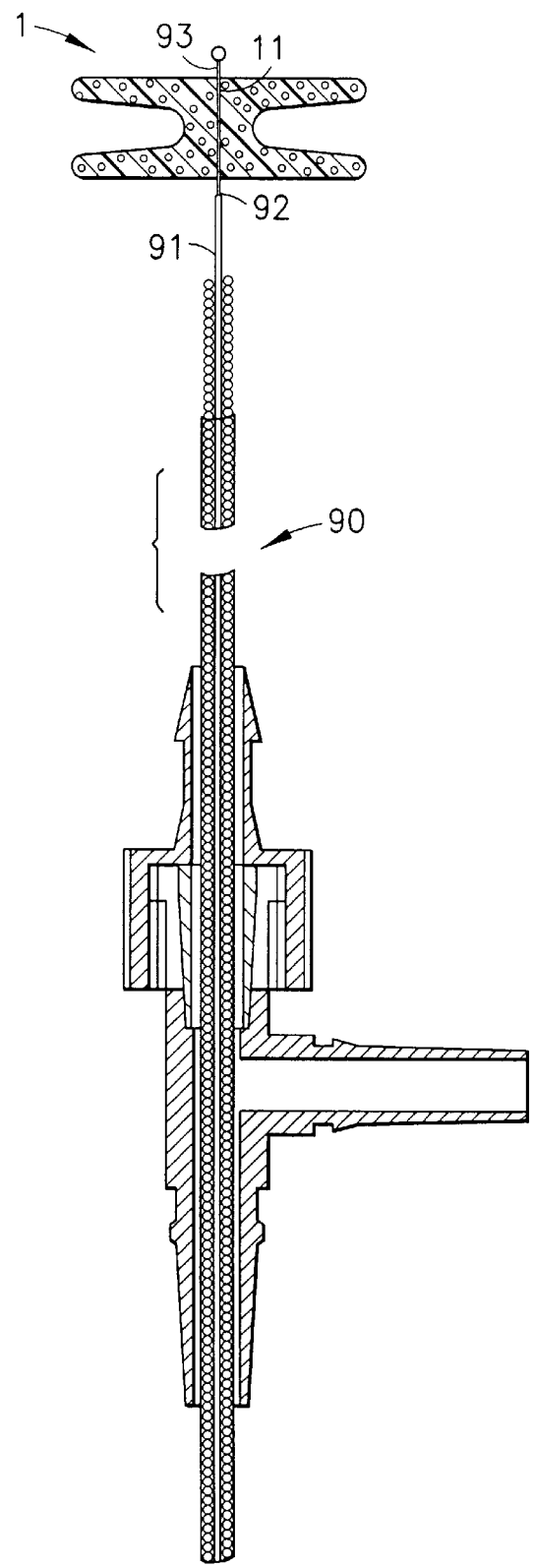
FIG. 20 is a detail sectional elevational view of portion of the implant device shown in use carrying an occluder device.

Referring now to FIGS. 19 to 21 there is shown an implant device 90 for deployment of the occluder devices in use. The implant device 90 has a catheter 91 within which is slidably received a guide wire 92. At an outer free end of the guide wire 92 is a gripper 93 (FIG. 21). The gripper 93 has a collar 94 with a number of slots 95 at an outer end of the collar 94 dividing the outer end of the collar 94 into a number of flaps 96. A bulbous head 97 at an outer end of the wire 92 is moveable through the collar 94 to move the flaps 96 outwardly to grip an occluder device. In use, with the head 97 in an advanced position out of the collar 94 the collar 94 can be inserted into the tubular sleeve 11 of the body of the occluder device 1. The wire 92 is retracted drawing the head 97 into the collar 94 thus expanding the flaps 96 to grip an inner surface of the tubular sleeve 11 of the occluder device 1. The occluder device 1 is thus firmly gripped and can be deployed in a defect in the usual manner. Once it has been correctly positioned the collar 94 is released and the wire 92 retracted leaving the occluder device 1 in the defect.

FIGS. 22 and 23 show another occluder device 100 having a body member with a cylindrical neck 101 with disks 102, 103 at each end. In this case, the width of the neck 101 is chosen such that it is equal to or greater than the greatest width of the opening or defect. In this way the device 100 will fill the opening and self-center within the opening.

FIG. 24 shows another occluder device 110. In this case, the occluder device 110 has a body member with a neck 111 which is essentially star-shaped in section having a central neck portion with a plurality of ribs 112 extending radially outwardly therefrom. The width across opposite ribs 112 is such that it is greater than or equal to the maximum width of the opening into which the occluder 110 is to be mounted for centering the neck of the body member in the opening.

It will be appreciated that the occluder device according to the present invention has a number of advantages over the known occluder devices. Residual shunts which is the incomplete closure of a target opening can be caused by the fact that the prior art devices are constructed with a metallic element in combination with polymeric sections forming the web or membrane. Anchoring is typically achieved through straining the metallic elements. The device of the present invention outlines a device wherein anchoring is achieved through compressing a polymer which can more readily adapt to the shape of the targeted opening. The device of the present invention will self-center to achieve a balance of compressive stresses throughout a cross-sectional area.

Further, the prior art closure devices use metallic elements to provide anchoring. Particularly when used for closure of septal defects, the inclusion of metal elements that are electrically conductive can disrupt the electrophysiological operation of the heart. This can have immediate or delayed impact during the life of the patient. The device of the present invention alleviates this problem through the use of foamed polymers that would provide insulation and/or better matching of impedance with the native tissue.

It will be appreciated that the use of an open cell polymer foam to form the device according to the present invention enables the provision of a suitable occluder device to close an opening while at the same time allows the device to be significantly compressed for transcatheter deployment. Further, the inherent flexibility of the foam enables the body member and flanges of the device to conform to contours and configuration of the opening and the tissue walls at each side of the opening for a good fitting of the occluder at the defect. It will be appreciated that the foam material of the occluder is also readily easily molded or cut to a desired shape for closing a given opening. Also, conveniently the foam material of the occluder will deform to accommodate other important cardiac structures in the proximity of the defect without causing damage to these cardiac structures.

I claim:

1. A transcatheter occluder device for closing an opening in a tissue wall or a vessel wall, the device comprising:

a body member formed substantially from an open cell polymer foam material which is self-supporting to hold a predetermined occluder shape and is resiliently compressible for transcatheter deployment;

the material being a biologically compatible material or coated with a biologically compatible material;

the body member having means for closing the opening; and the body member having means for retaining the body member in the opening.

2. The device as claimed in claim 1 further comprising means for engaging a side edge of the opening for centering the body member.

3. The device as claimed in claim 1 wherein at least a portion of a periphery of the body member is engagable with a side edge of the opening.

4. The device as claimed in claim 1 wherein the body member has a cross-sectional area that is at least the same size as a cross-sectional area of the opening.

5. The device as claimed in claim 1 wherein the body member is shaped to correspond to the shape of the opening.

6. The device as claimed in claim 1 wherein the body member has a cylindrical shape.

7. The device as claimed in claim 1 wherein the body member comprises a number of outwardly projecting ribs on a surface of the body member, said ribs being engagable with an edge of the opening in use.

8. The device as claimed in claim 1, wherein the retaining means comprises a pair of disks each of larger size than the opening, one of said disks being mounted at each end of the body member.

9. The device as claimed in claim 1, wherein the retaining means comprises a plurality of retaining fingers extending laterally outwardly at each end of the body member.

10. The device as claimed in claim 1 wherein the device further comprises radiopaque means to facilitate viewing of the device during deployment.

11. The device as claimed in claim 1 wherein the body member further comprises grip means engagable with a guide wire for movement of the device through a catheter for deployment.

12. The device as claimed in claim 1, further comprising a tubular sleeve mounted on the body member, the sleeve having a bore and being adapted to engage a clamp on a guide wire to facilitate movement of the device through a catheter for deployment, said clamp comprising a split collar through which the guide wire passes and an enlarged head at an outer end of the guide wire which is moveable through the collar to expand the collar within the bore of the sleeve to releasably clamp the collar within the sleeve of the body member.

13. The device as claimed in claim 1, further comprising a lug mounted on the body member which is adapted to releasably engage a collet at a distal end of a guide wire to facilitate movement of the device through a catheter for deployment.

14. The device as claimed in claim 1, further comprising an eye on the body member which is adapted to releasably engage a hook-shaped member at an outer end of a guide wire to facilitate movement of the device through a catheter for deployment.

* * * * *